(12) United States Patent
Dhombres et al.

(10) Patent No.: US 11,069,445 B2
(45) Date of Patent: Jul. 20, 2021

(54) MEDICAL DIAGNOSIS ASSISTANCE METHOD

(71) Applicants: UNIVERSITE PIERRE ET MARIE CURIE (PARIS 6), Paris (FR); CENTRE NATIONAL DE LA RECHERCHE SCIENTIFIQUE, Paris (FR); ASSISTANCE PUBLIQUE—HOPITAUX DE PARIS, Paris (FR)

(72) Inventors: Ferdinand Dhombres, Paris (FR); Jean-Marie Jouannic, Paris (FR); Eric Jauniaux, London (GB); Pascal Malengrez, Paris (FR); Paul Maurice, Paris (FR)

(73) Assignees: SORBONNE UNIVERSITE, Paris (FR); INSERM (INSTITUT NATIONAL DE LA SANTE ET DE LA RECHERCHE MEDICALE), Paris (FR); UCL BUSINESS PLC, London (GB); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 859 days.

(21) Appl. No.: 15/742,908

(22) PCT Filed: Jul. 1, 2016

(86) PCT No.: PCT/EP2016/065492
§ 371 (c)(1),
(2) Date: Jan. 9, 2018

(87) PCT Pub. No.: WO2017/009070
PCT Pub. Date: Jan. 19, 2017

(65) Prior Publication Data
US 2018/0218788 A1     Aug. 2, 2018

(30) Foreign Application Priority Data
Jul. 10, 2015   (FR) ...................................... 1556591

(51) Int. Cl.
*G16H 50/20*     (2018.01)
*A61B 8/08*      (2006.01)
*G16H 15/00*     (2018.01)
*A61B 5/00*      (2006.01)

(52) U.S. Cl.
CPC ........... *G16H 50/20* (2018.01); *A61B 8/0866* (2013.01); *A61B 5/4343* (2013.01); *A61B 8/5215* (2013.01); *G16H 15/00* (2018.01)

(58) Field of Classification Search
CPC .............................. G16H 50/20; A61B 8/0866
USPC ......................................................... 702/19
See application file for complete search history.

(56) References Cited

U.S. PATENT DOCUMENTS

2007/0237377 A1   10/2007  Oosawa
2014/0012790 A1    1/2014  Oberkampf et al.

OTHER PUBLICATIONS

These/Universite et al.: "Modelisation des signes dans les ontologies biomedicales pour l'aide au diagnostic" These soutenue a la faculte de medecine de Rennes 1, ANNEE 2013, Ecole doctorale vie-Agro-Sante (VAS) Presentee par Mme. Valerie Bertaud-Gounot PU-PH—Dec. 20, 2013, XP055252158.
International Search Report, dated Sep. 5, 2016, from corresponding PCT/EP2016/065492 application.

*Primary Examiner* — Jerry Lin
(74) *Attorney, Agent, or Firm* — Nixon & Vanderhye

(57) ABSTRACT

Disclosed is a method for assistance with the establishment of a diagnosis of a patient, starting from at least one identified sign, and based on a computerized knowledge database including a medical ontology. The medical ontology includes: a list of signs forming a "sign" class; a list of pathological states forming a "pathological state" class; and a first set of logical relationships between the signs and the pathological states, each logical relationship establishing a correlative link between a sign and a pathological state. The method includes: a step of searching for potential pathological states, linked to at least one of the identified signs by the first set of logical relationships; and a step of identifying potential signs in which, for each potential pathological state, all of the signs linked by a correlative link to the potential pathological state are identified by the first set of logical relationships.

15 Claims, 5 Drawing Sheets

MEDICAL DIAGNOSIS ASSISTANCE METHOD

TECHNICAL FIELD

The invention is situated within the field of assistance with the establishment of a medical diagnosis. It applies in particular, but not exclusively, to assistance with the diagnosis of ectopic pregnancies by means of an ultrasound examination. More precisely, the invention relates to a method for assistance with the establishment of a diagnosis of a patient, starting from an identified sign, based on a computerized knowledge database comprising a medical ontology.

STATE OF THE ART

Ultrasound technology is a technology for acquisition of images that is relatively low-cost, and considered as painless and non-invasive for the patient and the foetus. Nowadays its use is widespread throughout the world, both in the field of obstetrics and in the field of gynaecology.

In the field of obstetrics, prenatal screening for foetal anomalies by ultrasound has grown substantially in the last thirty years. In the majority of developed countries, this screening is based on carrying out one or two routine examinations, carried out at around five and seven months of amenorrhea by an operator, for example a doctor, a midwife, a radiologist or a sonographer. A reference set of standardized ultrasound cross-sections has progressively been proposed, so as to scan the foetal organs and there detect the main signs likely to affect them. These signs relate, for example, to an anomaly of a foetal organ, such as a malformation or delayed growth, or an anomaly in the quantity of amniotic fluid. An excess of amniotic fluid (hydramnios) can be the first warning sign of a foetal disorder. In the situation where one of the ultrasound cross-sections does not correspond to the usual image, in other words when the presence of a symptom is suspected, an immediate or deferred check is generally carried out by an expert operator. Similarly, analysis by an expert may be recommended in the case of family history, for example in the case of a history of malformation, a couple having a high risk of genetic anomaly, or of maternal pathology prior to pregnancy involving a risk of embryo-foetopathy. Generally, a detailed examination, carried out by an expert, is recommended in approximately 15 to 20% of pregnancies. The role of the expert is then to invalidate or confirm the existence of one or more anomalies, then to gather evidence contributing to the establishment of a diagnosis and a prognosis.

The operator responsible for carrying out the prenatal diagnosis by ultrasound is more or less experienced depending on the country and healthcare establishment. Most of the time, and in particular in emergency gynaecological facilities, young doctors with little experience in ultrasound are involved in a primary health care setting. The risk is that the first signs are not identified and that the patient is not referred to an expert in time.

Moreover, the present state of knowledge about obstetric pathology leads to great complexity in establishing a diagnosis. The number of rare diseases (approximately 6000), the number of developmental anomalies (approximately 1000) and the number of signs (approximately 8000 postnatally), which are increasingly accessible prenatally with the improvement of imaging techniques, show that even an expert practitioner cannot master all of the knowledge in the field.

In order to effectively manage all this knowledge, expert systems have been developed. These expert systems comprise a facts base, in this case of the signs and the pathological states, a rules base, and an inference engine. In this case, the facts correspond to signs and pathological states, and the rules correspond to correlative links between the signs and the pathological states. The inference engine is similar to an artificial intelligence. It uses the different facts and the rules connecting these facts to generate new facts, until a response that best satisfies them is arrived at. A drawback of the expert systems is that a result, i.e. a diagnosis, can only be provided if all of the necessary information is available. Now, this information cannot always be identified by a practitioner with little experience. In practice, the expert systems can thus facilitate the establishment of a diagnosis by an expert doctor, but cannot generally assist an operator having little experience in carrying out their examination with a view to a diagnosis being established, subsequently, by an expert doctor.

In the field of gynaecology, ultrasound has for many gynaecologists become the natural extension of the clinical gynaecological examination. In particular, it makes it possible to diagnose the most frequent gynaecological pathologies, such as endometriosis, ovarian cysts (benign or malignant), uterine fibroids, uterine adenomyosis or to investigate menopausal breakthrough bleeding. When pelvic ultrasound is carried out by an experienced operator, it leads to high diagnostic relevance.

However, as for prenatal screening for foetal anomalies, in practice the quality of the diagnosis is mediocre due, on the one hand, to inadequate training of the operators and, on the other hand, to the absence of a defined to examination protocol, unlike that which can be observed in the field of obstetrics.

DISCLOSURE OF THE INVENTION

A purpose of the invention is, in particular, to overcome all or some of the abovementioned drawbacks.

In particular, a purpose of the invention is to allow the operators carrying out a medical examination to be assisted in collecting all the information necessary for making a reliable diagnosis. This means collecting information not only to support the diagnosis established, but also to rule out other possible diagnoses.

In particular, the invention is aimed at allowing operators with little experience and knowledge in the field considered, to collect all the information necessary to allow an expert to make a reliable diagnosis.

The invention is based on the use of a computerized knowledge database comprising a medical ontology. Generally, a medical ontology constitutes a logical representation of the knowledge in the medical field, or in a particular medical field. Different concepts, such as signs, organs, pathological states (diseases or syndromes) are linked to one another or interlinked by means of semantic relationships. The ontology is generally modelled in a web-standard language that can be interpreted by computer, which makes it possible to carry out automatic procedures. The main advantage of the ontologies is being able to link heterogeneous data, allowing the processing of a large quantity of data, and being able to be enriched with new data without calling the data structure into question.

More precisely, a subject of the invention is a method for assistance with the establishment of a diagnosis of a patient, starting from at least one identified sign, and based on a computerized knowledge database comprising a medical ontology, the medical ontology comprising:
- a list of signs forming a "sign" class,
- a list of pathological states forming a "pathological state" class, and
- a first set of logical relationships between the signs and the pathological states, each logical relationship establishing a correlative link between a sign and a pathological state, the method comprising:
- a step of searching for potential pathological states, in which all of the pathological states linked by a correlative link to at least one of the identified signs are sought in the "pathological state" class by means of the first set of logical relationships, said pathological states forming the potential pathological states, and
- a step of identifying potential signs, in which for each potential pathological state, all of the signs linked by a correlative link to said potential pathological state are identified in the "sign" class by means of the first set of logical relationships, said signs forming the potential signs.

In the present patent application, the term "sign" denotes a phenomenon linked to the state of a patient. In particular, it covers the concepts of "functional sign", "clinical sign" and "paraclinical sign". A functional sign, also called a "symptom", denotes a phenomenon as felt and expressed subjectively, qualitatively or quantitatively by the patient. It is, for example, fatigue, a pain or a cough. A clinical sign is a sign observed during the clinical examination of a patient. It is noted objectively, whether the patient perceives it or not. It is, for example, a heart murmur, an abnormal reflex during a neurological examination, a crepitus phenomenon observed in the pulmonary field, or a drunken gait of a patient walking with eyes closed. A paraclinical sign is a sign observed using an instrument. It is, for example, a biological sign, a histological sign (pathological anatomy of a cancer, for example), or an imaging sign, i.e. a sign observed during the interpretation of a medical image. A medical image can be obtained by different image-acquisition techniques such as radiography, echography, computerized tomography examination or magnetic resonance imaging.

In the present patent application, the term "pathological state" denotes a state of alteration in the functions, the morphology or the health of an organ or organism the cause of which is known or unknown, and which is characterized by the presence or absence of one or more signs. It should be noted that the pathological state is denoted by the term "disease" when the cause is known, and by the term "syndrome" when it is unknown.

The method according to the invention thus makes it possible, to starting from one or more identified signs, to arrive at all of the pathological states potentially affecting the patient, and to list all of the signs correlated with each of these possible pathological states, in order to offer the practitioner a list of verifiable signs, allowing them, after analysis, to select one or more pathological states potentially affecting the patient.

According to a first embodiment variant, in the case where several identified signs are used in the method, the step of searching for potential pathological states is carried out by considering each identified sign individually. The step of searching for potential pathological states then consists of searching, in the case of each identified sign, for all of the pathological states linked by a correlative link to the identified sign considered, the different sets of pathological states thus found forming the potential pathological states. The step of identifying potential signs can be carried out several times, after each search for pathological states linked to one of the identified signs, or only once, when all the potential pathological states have been found.

According to a second embodiment variant, the step of searching for potential pathological states is carried out by considering all of the identified signs collectively. The step of searching for potential pathological states then consists of searching for all of the pathological states linked by a correlative link to each of the identified signs.

According to a particular embodiment, the first set of logical relationships comprises logical relationships according to each of which a sign is indicative of at least one pathological state. In other words, a logical relationship can take the following form: "Sign A is indicative of pathological state B". A logical relationship can link a single sign to a single pathological state. When a given sign is indicative of several pathological states, a multiplicity of logical relationships link this sign to the pathological states. The ontology makes it possible to represent a logical relationship defining several links between a given sign and pathological states. The logical relationship then takes the following form, for example: "Sign C is indicative of the pathological states D, E and F". Other types of logical relationships are also possible. For example, signs are never observed in certain pathological states. The corresponding logical relationship can then take the following form, for example: "Sign G is indicative of the absence of pathological state H". It is possible to assign to each logical relationship a coefficient representative of the probability that a sign is associated with a pathological state. The logical relationship then takes the following form, for example: "Sign J is present in 80% of cases of pathological state K".

Pathological states can have certain correlations with one another, in particular kindship relationships. In other words, certain pathological states can be constitutive of one or more pathological states. This is referred to as order between the pathological states. For a given pathological state of order m, where m is a strictly positive natural integer, all the pathological states to which it belongs form parent pathological states of order p, with p a natural integer strictly greater than m. By way of example, the pathological state "common cold" can be considered as a pathological state of order one, constitutive of a pathological state of order two, "viral infection of the nose". This pathological state of order two is itself constitutive of a pathological state of order three, "viral infection". This pathological state is constitutive of a pathological state of order four, "infectious disease".

Thus, according to a particular embodiment, the ontology also comprises a second set of logical relationships between pathological states of the "pathological state" class, each logical relationship defining a kinship link between a given pathological state and a parent pathological state of this given pathological state, the step of searching for potential pathological states comprising:
- searching for potential pathological states of order one, in which all of the pathological states indicated by at least one of the identified signs are sought, said pathological states forming the potential pathological states of order one, and
- searching for potential pathological states of order two to N, where N is a natural integer greater than or equal to two, the search for potential pathological states of order n, where n is a natural integer comprised between two and N, comprising, in the case of each potential pathological state of order n−1, a search for all of the parent pathological states of this potential pathological state of order n−1 by means of a second set of logical relationships, said parent pathological states forming the potential pathological states of order n, the step of identifying potential signs comprising an identification of all of the signs indicative of a potential pathological state of order one and/or a potential pathological state of order n.

The search for pathological states of an order greater than order one is limited by the number N. This number N must be determined so as to scan a sufficient and reasonable set of pathological states. The number N can thus be fixed as a function of the medical ontology considered, and in particular as a function of the number of pathological states in this ontology, or as a function of the number of potential pathological states identified in the corresponding step. The number N is, for example, comprised between two and four.

Advantageously, the step of identifying potential signs comprises a classification of these potential signs, according to which all of the potential signs indicative of a potential pathological state of order m, where m is a natural integer comprised between one and N, form the potential signs of order m. In other words, all the potential signs directly identified from a potential pathological state of order n are classified as potential signs of order n. To the extent that the same sign can be indicative of different pathological states, certain identical signs can be classified with different orders. It is then possible to retain only one of these signs, preferably that associated with the lowest order.

In order to help the practitioner to verify the different potential signs, it is possible to indicate to them the technical methods making it possible to observe these potential signs. Such is in particular the case when the signs can be observed by medical imaging. The medical ontology can then also comprise:

a list of technical methods for acquisition of medical images forming an "imaging" class, each technical method for acquisition of a medical image defining a type of technology for acquisition of medical images, and a positioning of the medical image on the patient, and a third set of logical relationships between the signs and the technical methods for acquisition of medical images, each logical relationship defining a technical method for acquisition of a medical image making it possible to observe a sign, the method also comprising:

a step of identifying technical methods for acquisition of interest, in which for each potential sign, all of the technical methods for acquisition of medical images making it possible to observe said potential sign are identified in the imaging class by means of the third set of logical relationships, said technical methods for acquisition of medical images forming the technical methods for acquisition of interest.

The term "technical method for acquisition of a medical image", or more simply "method for acquisition", denotes a set of technical features making it possible to obtain a certain medical image, capable of being compared with a reference image or reference data. In particular, a method for acquisition can be defined by a type of technology for acquisition of medical images and a positioning of the medical image relative to the patient. By way of examples, a method for acquisition can be defined by the ultrasound technique, and a median sagittal section of the brain of the foetus, or a section of the cephalic perimeter of the foetus, or a sagittal section of the patient's uterus.

The step of identifying technical methods for acquisition of interest can comprise a classification of these technical methods for acquisition of interest, according to which all of the technical methods for acquisition of medical images making it possible to observe a potential sign of order m form the technical methods for acquisition of interest of order m.

The method for assistance with the establishment of a diagnosis according to the invention can comprise a step of constructing an examination protocol. The examination protocol essentially comprises an ordered list of technical methods for acquisition of interest to be offered to the practitioner for searching for potential signs. Preferably the technical methods for acquisition of interest are hierarchized according to their order, the technical methods for acquisition of interest of order m having priority over the technical methods for acquisition of interest of order m+1.

Several technical methods for acquisition of interest can have the same order. In this case, it is possible to prioritize the technical methods for acquisition of interest making it possible to observe the most potential signs. Thus, the method can be organized such that the technical methods for acquisition of interest of the same order are hierarchized according to their occurrence among all of the technical methods for acquisition of interest of this order, or among all of the technical methods for acquisition of interest of the different orders.

The method according to the invention can also comprise a step of displaying the technical methods for acquisition of interest.

The method can also comprise:

a step of selecting technical methods for acquisition of interest to be implemented, in which at least one of the technical methods for acquisition of interest is selected, all of the technical methods for acquisition of interest selected forming the technical methods for acquisition to be implemented, and a step of acquisition of one or more medical images, each medical image being acquired according to one of the technical methods for acquisition to be implemented.

The step of acquisition of one or more medical images can be carried out more or less automatically. By way of example, in the case where all the technical methods for acquisition of interest involve the use of a magnetic resonance imaging device, the different images can be acquired without having to move the patient, and without the intervention of the practitioner.

The method for assistance with the establishment of a diagnosis of a patient can constitute an iterative method. In fact, once a set of potential signs have been identified, it is possible to verify the presence or absence of these signs, and to use them as constituting the identified signs for a new iteration of the method.

Thus, according to a particular embodiment, the method for assistance with the establishment of a diagnosis of a patient comprises a repetition of the steps of searching for potential pathological states, identifying potential signs and, if appropriate, a repetition of the steps of identifying technical methods for acquisition of interest, selecting technical methods for acquisition to be implemented and acquisition of one or more medical images. The method comprises, for example, on completion of each iteration of the step of acquisition of one or more medical images, a step of verifying the clinical state of the potential signs, these potential signs constituting the identified signs for a new iteration of the method, and a new iteration of the different steps of the method.

Still with the aim of assisting the practitioner in establishing the information making it possible to establish a diagnosis, the method according to the invention can provide the practitioner with reference images, both to make it possible for them to verify the normal or abnormal character of a phenomenon observed in the patient, or to help them to acquire images that can be used for the diagnosis.

The computerized knowledge database can thus also comprise a library of medical images, each medical image representing a sign, the method comprising, after the step of identifying potential signs, a step of searching for reference images in which, for at least one of the potential signs, all of the medical images representing said at least one potential sign are sought in the library of medical images, said medical images forming the reference images.

Each medical image can of course represent several signs. An image can represent a situation considered as normal or abnormal. In a particular embodiment, the step of searching for reference images comprises searching, in the case of at least one of the potential signs, for an image representing the potential sign in a normal situation, and an image representing the same potential sign in an abnormal situation.

According to a particular embodiment, the step of searching for reference images is carried out after the step of identifying technical methods for acquisition of interest, and comprises, in the case of at least one of the potential signs, searching for medical images representing said at least one potential sign and being acquired by means of one of the technical methods for acquisition of interest. The reference images are thus presented to the practitioner in the same form as that which are expected to be obtained during the acquisition of the images.

The medical ontology can relate to different medical fields and, in particular, to the fields of gynaecology and obstetrics. In particular, the medical ontology can relate to ectopic pregnancies.

A subject of the invention is also a device capable of implementing the method according to the invention. More precisely, the device can comprise a computer memory in which the knowledge database is stored, and processing means capable of carrying out the different steps, in particular the step of searching for potential pathological states, the step of identifying potential signs and, if appropriate, the step of identifying technical methods for acquisition of interest.

According to a particular embodiment, the device also comprises means for acquisition of medical images capable of acquiring images according to at least one of the technical methods for acquisition of medical images of the imaging class.

A subject of the invention is also a computer program comprising computer-executable instructions for implementing the method for assistance with the establishment of a diagnosis of a patient as described above.

Finally, a subject of the invention is a computer medium comprising computer-executable instructions for implementing the method described above.

DESCRIPTION OF THE FIGURES

Other advantages and features of the invention will become apparent on reading the detailed description of implementations and embodiments that are in no way limitative, with respect to attached drawings, in which.

DESCRIPTION OF EMBODIMENTS

As the embodiments described below are in no way limitative, it is possible, in particular, to consider variants of the invention comprising only a selection of characteristics described hereinafter, in isolation from the other characteristics described (even if this selection is isolated within a phrase containing these other characteristics), if this selection of characteristics is sufficient to confer a technical advantage or to differentiate the invention from the state of the prior art. This selection comprises at least one preferably functional, characteristic without structural details, or with only a part of the structural details if this part alone is sufficient to confer a technical advantage or to differentiate the invention from the state of the art.

It is recalled that the term "sign" denotes any phenomenon linked to the state of a patient and covers, in particular, the concepts of "functional sign", "clinical sign" and "paraclinical sign". The term "pathological state" relates to a state of deterioration in the functions, in the morphology or in the health of an organ or organism, being manifested by the presence or absence of one or more signs. The term "technical method for acquisition of a medical image", denotes a set of technical features making it possible to obtain a medical image capable of being compared with a reference image or with reference data.

Figure 1:
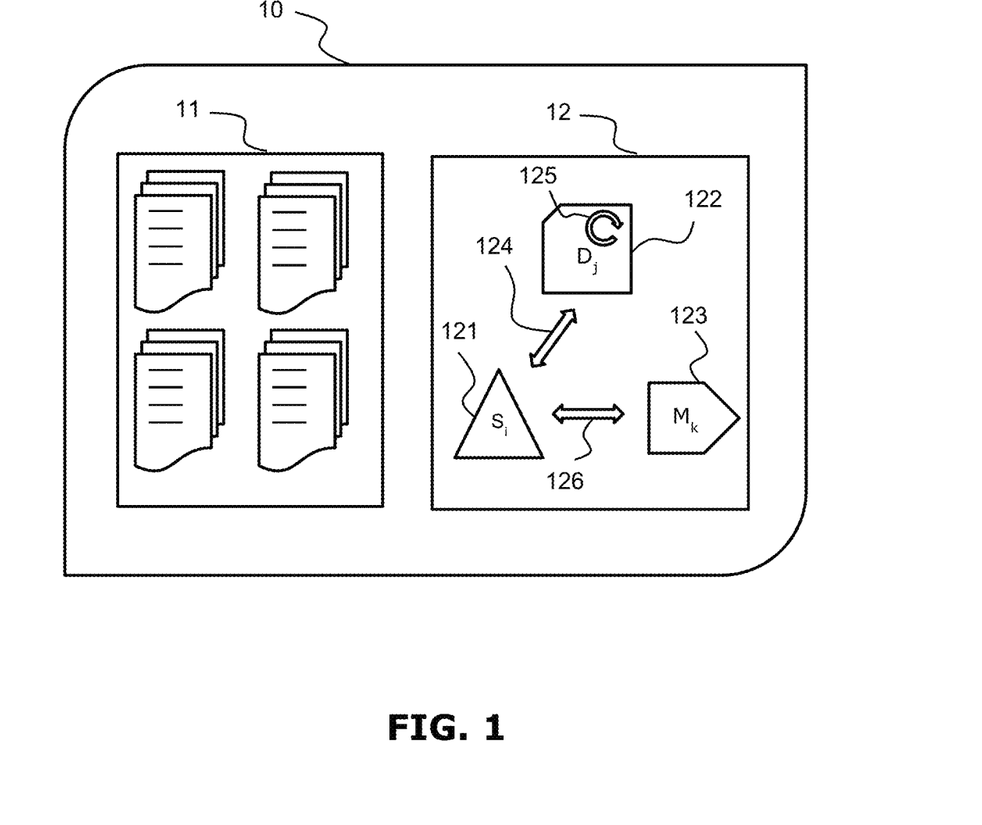
FIG. 1 diagrammatically represents an example of a computerized knowledge database on which the method for assistance with the establishment of a diagnosis according to the invention is based.

FIG. 1 diagrammatically represents a computerized knowledge database on which the method for assistance with the establishment of a diagnosis according to the invention is based. The knowledge database 10 is for example stored in a memory of a computer or server, or on a removable storage medium, such as a compact disc (CD) or a USB stick. It comprises a library 11 of medical images and a medical ontology 12. Each medical image represents one or more signs, and is associated with a label indicating different properties of the medical image. The label indicates, for example, the technique for acquisition of the medical image (CT or computed tomography imaging, ultrasound, etc.), the organ of the patient represented, the positioning of the image relative to the patient, for example the cross-sectional plane in which the image is situated, in the case of a plane image, or the borders of the image, in to the case of a three-dimensional image. The label can also indicate the presence of each sign that can be observed in the associated image, and the clinical state of this sign. The clinical sign can, for example, take one of the following values: "normal state", "state varying from the normal", "malformation", "inflammation", "excrescence" etc. The library 11 of medical images comprises, for example, pairs or sets of medical images, representing a given sign for different clinical states. In particular, one of the images can represent the sign for a state considered as normal.

Figure 2:
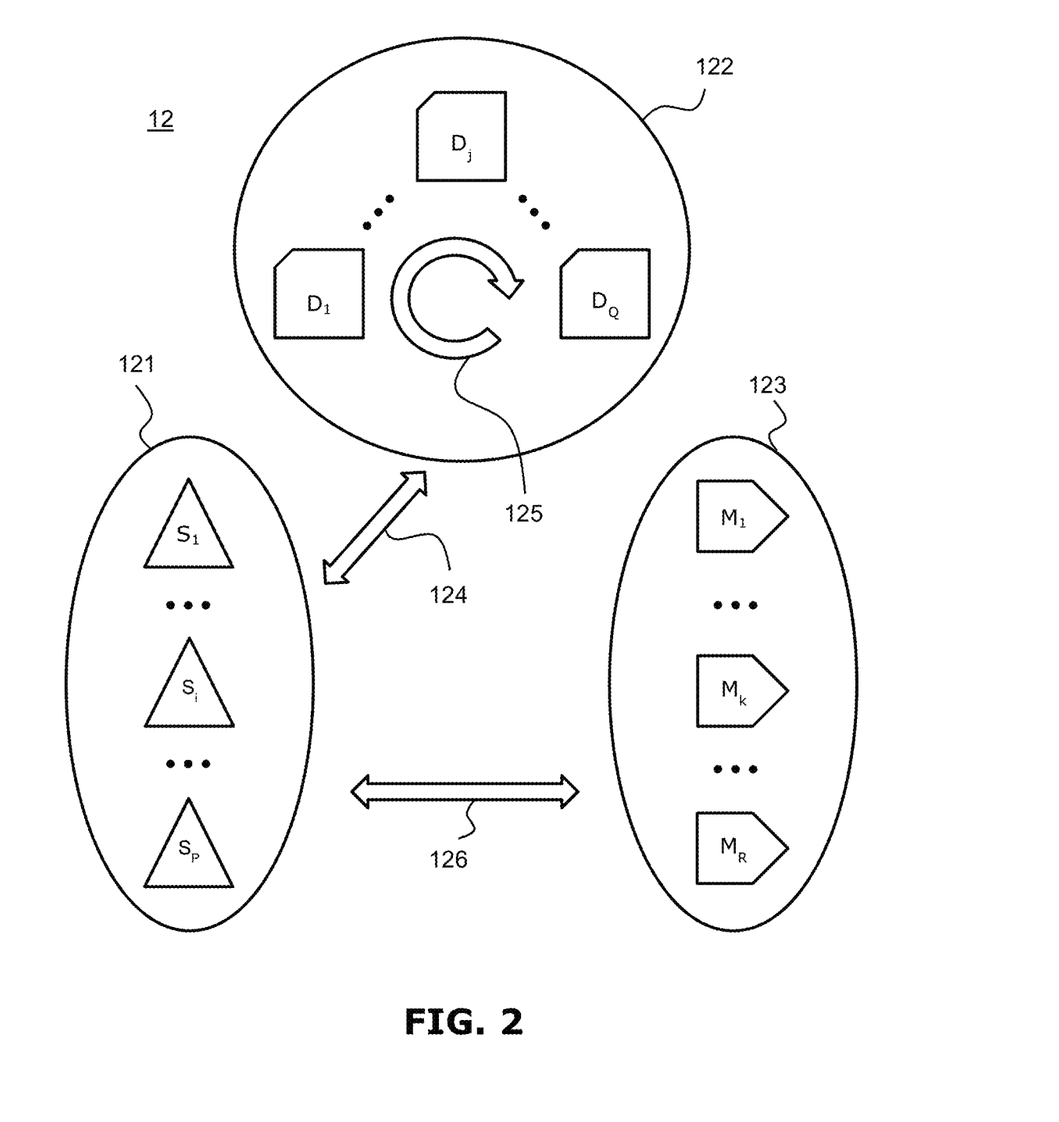
FIG. 2 represents an example of medical ontology.

FIG. 2 represents the medical ontology 12 in greater detail. The medical ontology 12 comprises a list 121 of signs, a list 122 of pathological states, and a list 123 of technical methods for acquisition of medical images. For the sake of ease of reading, the signs are denoted individually or globally by the reference $S_i$, where the subscript i is a natural integer comprised between one and P, the pathological states are denoted individually or globally by the reference $D_j$, where the subscript j is a natural integer comprised between one and Q, and the technical methods for acquisition of medical images are denoted individually or globally by the reference $M_k$, where the subscript k is a natural integer comprised between one and R. The integers P, Q and R are natural integers greater than or equal to two. They can be of the order of a few tens, a few hundred or even several thousand. All of the signs $S_i$ form a "sign" class, all of the pathological states $D_j$ form a "pathological state" class, and all of the technical methods for acquisition of medical images form an "imaging" class.

In addition, the medical ontology 12 comprises a first set 124 of logical relationships between the signs $S_i$ and the pathological states $D_j$, a second set 125 of logical relationships between the pathological states $D_j$, and a third set 126 of logical relationships between the signs $S_i$ and the technical methods for acquisition of medical images $M_k$. Each logical relationship of the first set 124 establishes a correlative link between a sign $S_i$ and a pathological state $D_j$, as explained in more detail with reference to FIG. 3. Each logical relationship of the second set 125 defines a kinship link between a given pathological state $D_j$, and a parent pathological state $D_l$ of this given pathological state as explained in more detail with reference to FIG. 4. Each logical relationship of the third set 126 defines a technical method for acquisition of a medical image $M_k$ making it possible to observe one of the signs $S_i$. A sign $S_i$ can be observable by means of several technical methods for acquisition of a medical image $M_k$. Moreover, a technical method for acquisition of a medical image $M_k$ can make it possible to observe several signs $S_i$.

Figure 3:
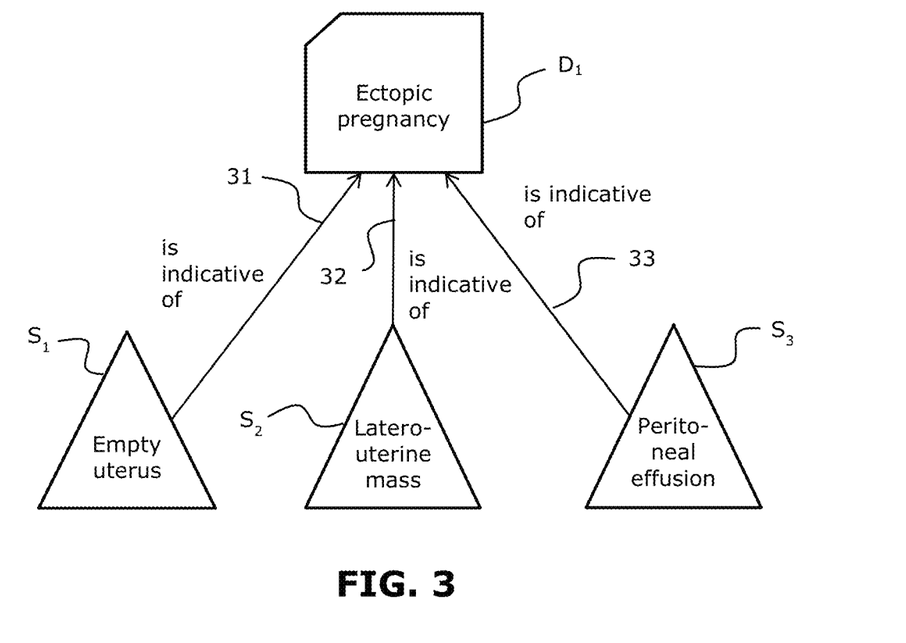
FIG. 3 shows an example of logical relationships between a pathological state and signs.

FIG. 3 shows an example of logical relationships between a pathological state $D_1$ and signs $S_1$, $S_2$, and $S_3$, in the field of gynaecology. By way of example, it is considered that the pathological state $D_1$ is an ectopic pregnancy and that the signs $S_1$, $S_2$ and $S_3$ are respectively an empty uterus, a latero-uterine mass, and peritoneal effusion. Each sign $S_i$ is indicative of the pathological state $D_1$. The logical relationships 31, 32, 33 are thus defined as a consequence. It is possible to assign to each logical relationship a coefficient representative of the probability that a sign is associated with a pathological state. During the execution of the method according to the invention, potential pathological states can thus be prioritized over others.

Figure 4:
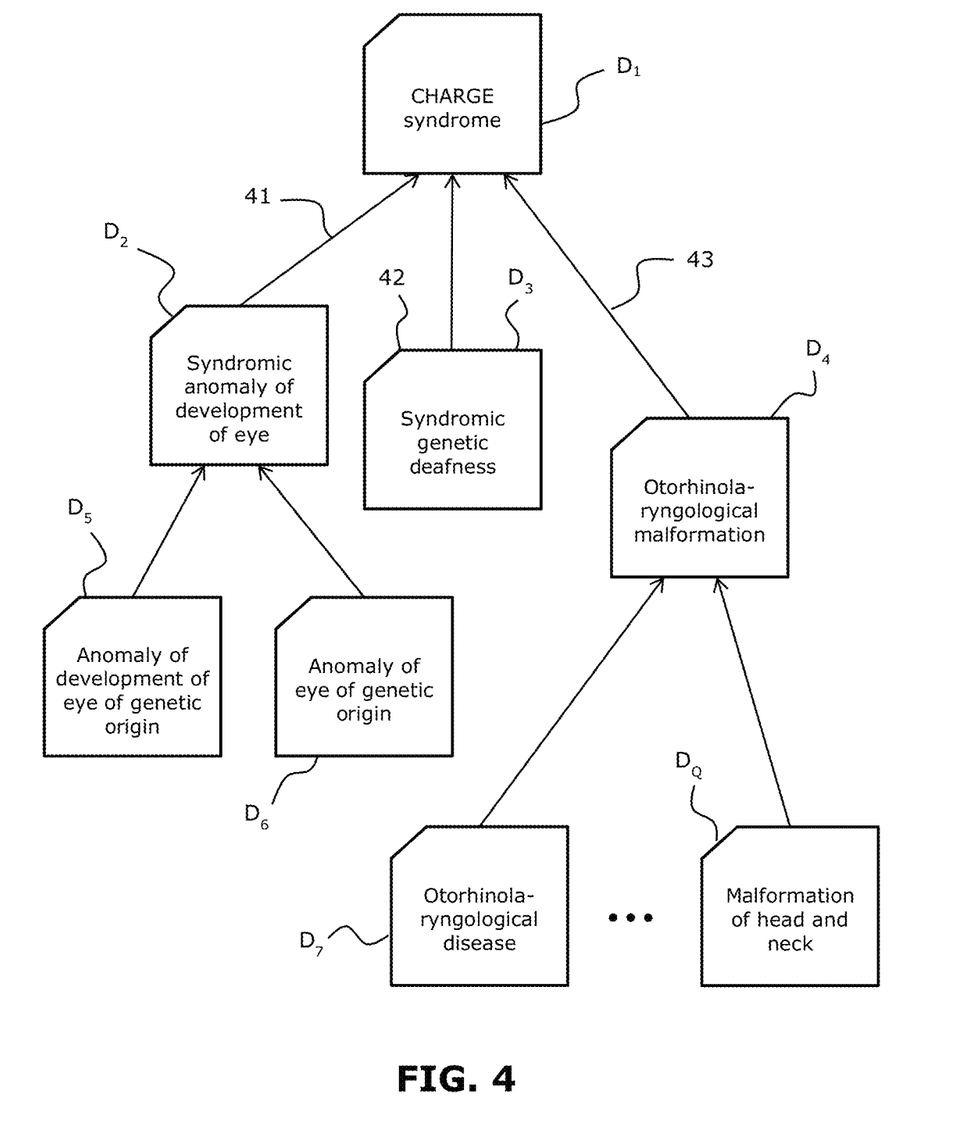
FIG. 4 shows an example of logical relationships between several pathological states.

FIG. 4 shows an example of logical relationships between several pathological states in the field of foetal medicine. By way of example, it is assumed that the pathological state $D_1$ is CHARGE syndrome, and that it is a pathological state of order one. This pathological state $D_1$ is the daughter pathological state of three pathological states $D_2$, $D_3$ et $D_4$, corresponding respectively to a syndromic anomaly of the development of the eye, a syndromic genetic deafness, and an otorhinolaryngological malformation. These pathological states $D_2$-$D_4$ are called parent pathological states, or parent first pathological states, in so far as they are directly linked to pathological state $D_1$. They form pathological states of order two. The pathological state $D_2$ (syndromic anomaly of the development of the eye) is the child of two parent pathological states $D_5$ et $D_6$, corresponding respectively to an anomaly of the development of the eye of genetic origin and an anomaly of the eye of genetic origin. These pathological states constitute pathological states of order three vis-à-vis the pathological state $D_1$. Similarly, the pathological state $D_4$, (otorhinolaryngological malformation), is the child pathological state of the pathological states $D_7$ (otorhinolaryngological disease) to $D_Q$ (malformation of the head and neck). In a similar manner to the relationships between the signs and the pathological states, the logical relationships between the pathological states can comprise coefficients representative of a probability of kinship.

Figure 5:
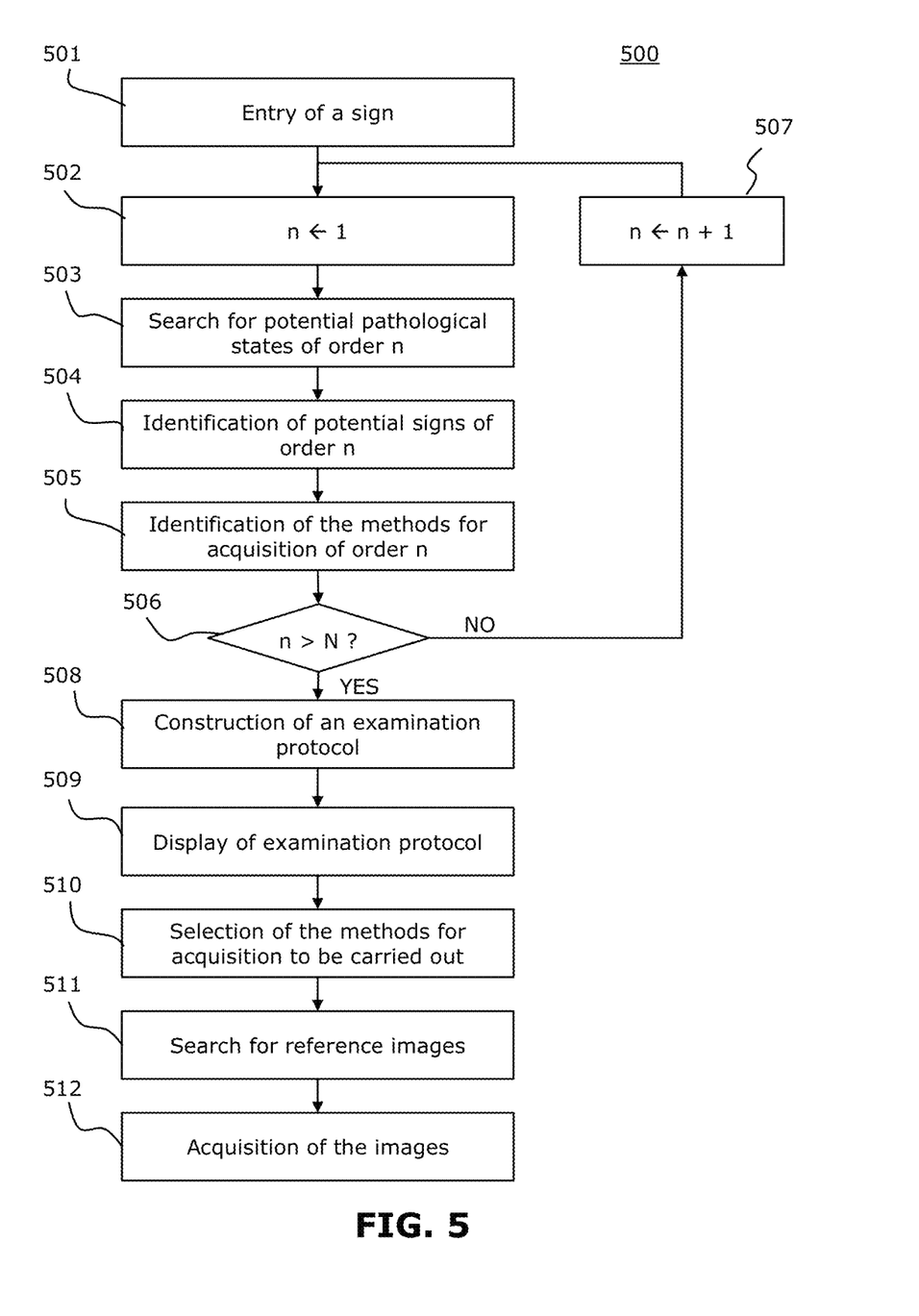
FIG. 5 represents an example of a method for assistance with the establishment of a diagnosis of a patient according to the invention.

FIG. 5 represents an example of a method for assistance with the establishment of a diagnosis of a patient according to the invention. The method 500 comprises a first step 501, in which one or more signs $S_i$ are entered by an operator into a device implementing the method, such as a computer. These signs can typically have been identified or assumed by an operator. They are thus called "identified signs".

In subsequent steps, potential pathological states of order one to N are sought. To this end, in a second step 502 a variable n takes the value one.

In a subsequent step 503, all of the potential pathological states $D_j$ of order n are sought in the "pathological state" class. During the first iteration of this step 503, where n has the value one, the search is carried out by means of the first set 124 of logical relationships. During subsequent iterations of step 503, where n takes an integer value comprised between two and N, the search is carried out by means of the second set 125 of logical relationships. Step 503 of searching for potential pathological states $D_j$ results in a list of potential pathological states of different orders. The information relating to the order of each pathological state can be retained, with the objective of hierarchization, as explained below.

In a fourth step 504, all of the potential signs $S_i$ of order n indicative of a potential pathological state $D_j$ of order n are identified in the signs class. This step 504 is carried out by means of the first set 124 of logical relationships. The step 504 can comprise a classification of the identified potential signs S, as a function of the order of the potential pathological state $D_j$ which has revealed them. Advantageously, when a potential sign $S_i$ is identified for different orders, it is possible to retain only the potential sign of the lowest order.

In a step 505, all of the technical methods for acquisition of the medical images $M_k$ making it possible to observe the potential signs $S_i$ of order n are identified. More precisely, for each potential sign $S_i$ of order n, all the technical methods for acquisition of the medical images $M_k$ are identified in the sign class, by means of the third set 126 of logical relationships. These methods for acquisition are called technical methods for acquisition of interest. The step 505 can comprise a classification of the methods for acquisition of interest $M_k$ as a function of the order associated with the potential sign $S_i$ considered, so as to make it possible to classify these methods for acquisition $M_k$ according to whether they are more or less capable of showing potential signs $S_i$ close to the initial sign identified by the operator.

In a step 506, it is verified whether the search for potential pathological states, and their associated potential signs, has sufficiently explored possible pathways. In practice it is verified whether the variable n is less than or equal to N, or strictly greater than N. In the first case, this variable is incremented by one unit in step a 507, and steps 502 to 506 are reiterated with this new value of n. In the second case, the search for new potential pathological states, associated new potential signs, and associated new methods for acquisition of interest ends.

The method then executes a step 508 in which an examination protocol is constructed. This examination protocol consists of listing all of the technical methods for acquisition of interest $M_k$, preferably as a function of their classification. The examination protocol thus constructed can be displayed to the operator in a step 509.

In a step 510, the technical methods for acquisition of images to be implemented are selected from the technical methods of interest. The selection can be carried out by an operator, or automatically by an algorithm. It consists, for example, of selecting the methods for acquisition having the lowest order. Moreover, the methods for acquisition making it possible to observe the most potential signs over the same image, or involving the use of a single medical imaging device, can be selected to the detriment of methods for acquisition resulting in the observation of a single potential sign, or methods for acquisitions involving the use of different medical imaging devices.

In an optional step 511, one or more reference images can be sought as a function of the methods for acquisition to be implemented. Step 511 consists of searching, in the library 11 of medical images, for those corresponding to the technical methods for acquisition to be implemented, and which thus represent potential signs. This search can be carried out via the label associated with each image. The operator having to carry out the acquisition of the medical images thus has reference images to allow them to verify that the acquired image corresponds to that expected for the subsequent establishment of a diagnosis.

In a step 512, medical images are acquired. These medical images are acquired according to the technical methods for acquisition to be implemented. The acquisition of the images can be carried out by an operator, or automatically by one or more devices for acquisition of images.

Of course, the invention is not limited to the examples which have just been described and numerous adjustments can be made to these examples without exceeding the scope of the invention. In particular, the signs of the ontology cannot necessarily be observed by means of one image, but can consist of any type of phenomenon linked to the state of a patient, such as the patient's body temperature, or a physical or biochemical property of a body fluid of the patient. Thus, the step of identifying technical methods for acquisition of medical images can consist, more generally, of a step of identifying technical methods for acquisition of medical data. Furthermore, the different characteristics, forms, variants and embodiments of the invention can be combined together according to various combinations to the extent that they are not incompatible or mutually exclusive.

The invention claimed is:

1. A device-implemented method for assistance with the establishment of a diagnosis of a patient, comprising:
providing a device that incorporates a computerized knowledge database (10) of a medical ontology (12) that includes a first list (121) of signs (Si) forming a "sign" class, a list (122) of pathological states (Dj) forming a "pathological state" class, a first set (124) of logical relationships between the signs and the pathological states, each logical relationship of said first set (124) establishing a correlative link between a sign and a pathological state, a second list (123) of technical methods for acquiring medical images (Mk) forming an "imaging" class, each of said technical methods for acquiring medical images (Mk) defining a type of technology for acquisition of medical images and a positioning of the medical image on the patient, and a third set (126) of logical relationships between the signs and the technical methods for acquiring medical images (Mk), each logical relationship of said third set (126) defining a technical method for acquiring a medical image that makes possible an observation of a sign;
receiving, at the device from an operator of the device, one or more identified signs;
searching (503), carried out by the device, for potential pathological states, in which all of the pathological states linked by a correlative link to at least one of the identified signs are sought in the pathological state class by means of the first set (124) of logical relationships, said pathological states forming the potential pathological states;
identifying (504), carried out by the device, potential signs in which, for each potential pathological state, all of the signs linked by a correlative link to said potential pathological state are identified in the sign class by means of the first set (124) of logical relationships, said signs forming the potential signs; and
identifying (505), carried out by the device, technical methods for acquisition of interest, in which for each potential sign, all of the technical methods for acquiring medical images that make possible to observe said potential sign are identified in the imaging class by means of the third set (126) of logical relationships, said technical methods for acquiring medical images forming the technical methods for acquisition of interest.

2. The method according to claim 1, wherein the first set (124) of logical relationships comprises logical relationships according to each of which a sign (Si) is indicative of a pathological state (Dj).

3. The method according to claim 2,
wherein the medical ontology (12) also includes a second set (125) of logical relationships between pathological states of the pathological state class, each logical relationship of said second set (125) defining a kinship link between a given pathological state and a parent pathological state of the given pathological state,
wherein the step (503) of searching for potential pathological states includes the sub-steps of:
searching for potential pathological states of order one, in which all of the pathological states indicated by at least one of the identified signs are sought, said pathological states forming the potential pathological states of order one, and
searching for potential pathological states of order two to N, where N is a natural integer greater than or equal to two, the search for potential pathological states of order n, where n is a natural integer comprised between two and N, comprising, for each potential pathological state of order n−1, searching for all of the parent pathological states of this potential pathological state of order n−1 by means of the second set (125) of logical relationships, said parent pathological states forming the potential pathological states of order n,
and wherein the step (504) of identifying potential signs includes identifying all of the signs indicative of a potential pathological state of order one and/or a potential pathological state of order n.

4. The method according to claim 3, wherein the step (504) of identifying potential signs includes classifying said potential signs, according to which all of the potential signs indicative of a potential pathological state of order m, where m is a natural integer comprised between one and N, form the potential signs of order m.

5. The method according to claim 1, wherein the step (505) of identifying technical methods for acquisition of interest includes classifying the technical methods for acquisition of interest, according to which all of the technical methods for acquisition of medical images making it possible to observe a potential sign of order m form the technical methods for acquisition of interest of order m.

6. The method according to claim 5, further comprising: displaying the technical methods for acquisition of interest.

7. The method according to claim 5, further comprising: constructing (508) an examination protocol, in which the technical methods for acquisition of interest are hierarchized according to their order, the technical methods for acquisition of interest of order m having priority over the technical methods for acquisition of interest of order m+1.

8. The method according to claim 7, further comprising: displaying the technical methods for acquisition of interest.

9. The method according to claims claim 7, wherein the technical methods for acquisition of interest of a same order are hierarchized according to their occurrence among all of the technical methods for acquisition of interest of the order, or among all of the technical methods for acquisition of interest of orders different from the order.

10. The method according to claim 1, further also comprising:
displaying the technical methods for acquisition of interest.

11. The method according to claim 1, further comprising:
selecting (510) technical methods for acquisition to be implemented, in which at least one of the technical methods for acquisition of interest is selected, all of the technical methods for acquisition of interest selected forming the technical methods for acquisition to be implemented, and one or more medical images, each medical image being acquired according to one of the technical methods for acquisition to be implemented.

12. The method according to claim 1,
wherein the computerized knowledge database (10) also includes a library (11) of medical images, each medical image representing a sign, and
wherein the method further comprises, after the step (504) of identifying potential signs:
searching (511) for reference images in which, in a case of at least one of the potential signs, all of the medical images representing said at least one potential sign are sought in the library (11) of medical images, said medical images forming the reference images.

13. The method according to claim 12, wherein the step (511) of searching for reference images is carried out after the step (505) of identifying technical methods for acquisition of interest, and comprises, in the case of at least one of the potential signs, searching for medical images representing said at least one potential sign and being acquired by means of one of the technical methods for acquisition of interest.

14. The method according to claim 1, wherein the medical ontology (12) relates to ectopic pregnancies.

15. A non-transitory computer-readable medium on which are stored computer-executable instructions that, when executed by a computer, cause the computer to perform the method according to claim 1.

* * * * *